United States Patent
Takano et al.

(10) Patent No.: US 9,200,250 B2
(45) Date of Patent: Dec. 1, 2015

(54) METHOD FOR PRODUCTION OF DRY YEAST CONTAINING S-ADENOSYL-L-METHIONINE AND HAVING EXCELLENT STORAGE STABILITY, PRODUCT PRODUCED BY THE METHOD, AND MOLDED COMPOSITION OF THE DRY YEAST

(75) Inventors: Kentarou Takano, Niigata (JP); Shinyo Gayama, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 12/524,050

(22) PCT Filed: Jan. 23, 2008

(86) PCT No.: PCT/JP2008/050852
§ 371 (c)(1),
(2), (4) Date: Jul. 22, 2009

(87) PCT Pub. No.: WO2008/090905
PCT Pub. Date: Jul. 31, 2008

(65) Prior Publication Data
US 2010/0075403 A1    Mar. 25, 2010

(30) Foreign Application Priority Data

Jan. 25, 2007    (JP) .................. 2007-015257

(51) Int. Cl.
*C12N 1/16* (2006.01)
*C12N 1/18* (2006.01)
*A23L 1/30* (2006.01)
*C12N 1/04* (2006.01)

(52) U.S. Cl.
CPC .................. *C12N 1/18* (2013.01); *A23L 1/3012* (2013.01); *A23L 1/3016* (2013.01); *C12N 1/04* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,881,837 | B2 | 4/2005 | Deshpande et al. |
| 2002/0006450 | A1 | 1/2002 | Nakahara et al. |
| 2003/0138936 | A1 | 7/2003 | Mizuguchi et al. |

FOREIGN PATENT DOCUMENTS

| | | | |
|---|---|---|---|
| CN | 1335885 A | | 2/2002 |
| EP | 1 091 001 | | 4/2001 |
| EP | 1 281 752 A1 | | 2/2003 |
| JP | 52 48691 | | 4/1977 |
| JP | 54005092 | * | 1/1979 |
| JP | 59 51213 | | 3/1984 |
| JP | 60 181095 | | 9/1985 |
| JP | 60181095 | * | 9/1985 |
| JP | 61005711 | * | 2/1986 |
| JP | 61 91125 | | 5/1986 |
| JP | 61 227792 | | 10/1986 |
| JP | 1 49274 | | 10/1989 |
| JP | 1 49275 | | 10/1989 |
| JP | 3 501970 | | 5/1991 |
| JP | 4 21478 | | 4/1992 |
| JP | 6 30607 | | 4/1994 |
| JP | 2001 169797 | | 6/2001 |
| JP | 2002 17337 | | 1/2002 |
| JP | 2005 229812 | | 9/2005 |
| JP | 2005-229812 | * | 9/2005 |
| WO | 2005 084646 | | 9/2005 |

OTHER PUBLICATIONS

Shiozaki et al. Agric. Biol. Chem. 1984, 48(9), 2293-2300.*
Martin Del Valle. "Cyclodextrins and their uses: a review". Process Biochemistry, 2003, pp. 1-14.*
Shiozaki et al. Agric. Biol. Chem. 1984, 48(9), pp. 2293-2300.*
Sébastien Branchu, et al. "Hydroxypropyl-β-cyclodextrin Inhibits Spray-Drying-Induced Inactivation of β-Galactosidase", Journal of Pharmaceutical Sciences, vol. 88, No. 9, XP-002553774, Sep. 1, 1999, pp. 905-911.
Wu Junjie, et al., "The Advancement of Inclusive Technology of Cyclodextrin", Progress in Research of Cyclodextrin Clathration Technology, Journal of Xinjiang Normal University, vol. 24, No. 2, Jun. 2005, pp. 51-54 (with English abstract).

* cited by examiner

*Primary Examiner* — Vera Afremova
(74) *Attorney, Agent, or Firm* — Oblon, McClelland, Maier & Neustadt, L.L.P.

(57) ABSTRACT

The present invention relates to a method for producing a dry yeast containing S-adenosyl-L-methionine using a yeast having production capability of S-adenosyl-L-methionine, the method containing: adding a cyclodextrin compound to a yeast concentrate obtained from a fungus culture liquid of the yeast; and then drying the concentrate, an SAMe-containing dry yeast obtained by the production method, and a composition formed by molding the dry yeast. According to the present invention, a dry yeast containing S-adenosyl-L-methionine, which is useful as an aqueous physiologically active substance, in a high concentration excellent in storage stability and a composition obtained by molding the dry yeast can be produced conveniently and economically and can be brought into the market.

19 Claims, No Drawings

METHOD FOR PRODUCTION OF DRY YEAST CONTAINING S-ADENOSYL-L-METHIONINE AND HAVING EXCELLENT STORAGE STABILITY, PRODUCT PRODUCED BY THE METHOD, AND MOLDED COMPOSITION OF THE DRY YEAST

TECHNICAL FIELD

The present invention relates to a method for producing a dry yeast containing S-adenosyl-L-methionine (which is hereinafter referred to as SAMe) excellent in storage stability, using a yeast having production capability of SAMe, and a product produced by the production method. More specifically, it relates to a method for producing a dry yeast containing SAMe excellent in storage stability, using a yeast having production capability of the compound, in which a cyclodextrin compound is added to a yeast concentrate obtained from a fungus culture liquid of the yeast, and then the concentrate is dried, and relates to a dry yeast containing SAMe obtained by the production method and a composition formed by molding the dry yeast containing SAMe.

BACKGROUND ART

SAMe is a water soluble physiologically active substance that plays an important role as a methyl group donor in methylation reaction with various transmethylases within the living body, is found in most of cells in the human body, functions as a cofactor of various biochemical reactions, and is a substance that is necessary, for example, for maintenance of cartilage and biosynthesis of brain substances. Studies on functions of SAMe in recent years report curative effects on fatty liver, hyperlipemia, arteriosclerosis, insomnia and the like. SAMe is an important physiologically active substance and is widely used in the Western countries as a therapeutic medication for depression, liver disorder, arthritis and the like, or health foods.

Accordingly, there are strong demands on production and provision of SAMe at low cost with ease, and the known production methods of SAMe include a method of fermentative production using a culture medium containing L-methionine as a precursor (see, for example, Patent Documents 1 to 3 and Non-patent Documents 1 to 7), a method of enzymatically synthesizing SAMe with adenosine 5'-triphosphate (ATP) and L-methionine as substrates using a SAMe synthesizing enzyme (methionine adenosyltransferase), which is isolated and purified from microorganisms, such as a yeast (see, for example, Patent Documents 4 to 5 and Non-patent Documents 7 to 11), and a method of synthesis process (see, for example, Patent Document 6 and Non-patent Document 12).

In the enzymatic synthesis method, SAMe is enzymatically synthesized with adenosine 5'-triphosphate (ATP) and L-methionine as substrates using a SAMe synthesizing enzyme (methionine adenosyltransferase), which is isolated and purified from microorganisms, such as a yeast, and the method has such advantages that SAMe is accumulated in a large amount, and it is not necessary to extract SAMe from the fungus, as compared to the fermentative method, but has various problems, in which preparation of the enzyme is complicated, the resulting enzyme has weak activity, it is necessary to remove a inhibition substance, such as ATP degradation enzyme and ATP as the substrate is considerably expensive, and therefore, the method has not been subjected to practical use.

According to developments of gene engineering in recent years, the enzyme can be conveniently prepared by using cloned SAMe synthesizing enzyme gene (see, for example, Non-patent Documents 6 to 9) to solve the problem in preparation of the enzyme, but other practical problems, such as the use of expensive ATP as the substrate, have not yet been resolved.

Furthermore, SAMe is thermally unstable and is easily decomposed, and as a countermeasure thereto, various attempts have been made for improving the storage stability. For example, such methods are proposed that a composition of SAMe obtained by the aforementioned methods is purified by chromatography or the like, and formed into a salt with sulfuric acid or p-toluenesulfonic acid, a salt with butanedisulfonic acid, or the like, thereby stabilizing SAMe (see, for example, Patent Documents 1 to 3 and 7 to 11), and an additive is added to purified SAMe for stabilization (see, for example, Patent Documents 1 to 3 and 7 to 13), but large amounts of labor and cost are required therefor, and sufficient storage stability cannot be necessarily obtained thereby. Accordingly, it is difficult to provide SAMe, which is important as a therapeutic medication and health foods, at an economical price.

As a method for producing and providing SAMe at an economical price, such a method is reported that a dry yeast containing SAMe is produced by a fermentation method, but SAMe contained in a dry yeast produced cannot have sufficient storage stability (see, for example, Patent Document 14).

[Patent Document 1] JP-B-4-21478
[Patent Document 2] JP-B-6-30607
[Patent Document 3] European Patent No. 1,091,001
[Patent Document 4] JP-A-61-227792
[Patent Document 5] JP-A-2001-169797
[Patent Document 6] U.S. Pat. No. 6,881,837
[Patent Document 7] JP-A-59-51213
[Patent Document 8] JP-A-52-48691
[Patent Document 9] JP-B-1-49274
[Patent Document 10] JP-B-1-49275
[Patent Document 11] JP-T-3-501970
[Patent Document 12] JP-A-60-181095
[Patent Document 13] JP-A-61-91125
[Patent Document 14] JP-A-2005-229812
[Non-patent Document 1] Schlenk F., DePalma R. E., J. Biol. Chem., 229, 1037-1050 (1957)
[Non-patent Document 2] Shiozaki S., et al., Agric. Biol. Chem., 48, 2293-2300 (1984)
[Non-patent Document 3] Shiozaki S., et al., Agric. Biol. Chem., 53, 3269-3274 (1989)
[Non-patent Document 4] Kusakabe H., Kuninaka A., Yoshino H., Agric. Biol. Chem., 38, 1669-1672 (1974)
[Non-patent Document 5] Mudd S H., Cantoni G L., et al., J. Biol. Chem., 231, 481-492 (1958)
[Non-patent Document 6] Shiozaki S., et al., J. Biotechnology., 4, 345-354 (1986)
[Non-patent Document 7] Thomas D., Surdin-Kerjan Y., J. Biol. Chem., 262, 16704-16709 (1987)
[Non-patent Document 8] Markham G. D., et al., J. Biol. Chem., 255, 9082-9092 (1980)
[Non-patent Document 9] Markham D J., DeParisis J., J. Biol. Chem., 259, 14505-14507 (1984)
[Non-patent Document 10] Thomas D., Cherest H., et al., Mol. Cell. Biol., 8, 5132-5139 (1988)
[Non-patent Document 11] Jeongho Park, Junzhe Tai, Charles A. Roessner and A. Ian Scott., Bioorganic & Medical Chemistry, Vol. 4, No. 12, 2179-2185 (1996)

[Non-patent Document 12] Jose R. Mator, Frank M. Raushel, Chi-Huey Wong., Biotechnology and Applied Biochemistry., 9, 39-52 (1987)

DISCLOSURE OF THE INVENTION

An object of the present invention is to establish a convenient and economical production method of a dry yeast containing SAMe in a high concentration excellent in storage stability, and is to provide a dry yeast containing SAMe obtained by the production method and a composition extremely excellent in storage stability formed by molding the dry yeast.

As a result earnest investigations made by the inventors with respect to a method capable of producing economically a composition that contains SAMe at a high concentration, can be stored in a stable state for a prolonged period of time, and is excellent in performance, it has been found that the target dry yeast as a composition that contains SAMe in a high concentration and is excellent in storage stability can be produced conveniently with a high yield in such a manner that: SAMe is synthesized by using a yeast having SAMe production capability capable of being orally, and is accumulated in a high concentration in the fungus; the yeast is then separated from the culture liquid with a separation measure, such as centrifugation; a cyclodextrin compound is added to the resulting concentrate of the yeast; and the concentrate is then dried, whereby the present invention has been completed.

Accordingly, the present invention provides a method for producing a dry yeast containing SAMe in a high concentration excellent in storage stability and a molded article using the dry yeast in an efficient manner shown in the items (1) to (8) below.

(1) A method for producing a dry yeast containing S-adenosyl-L-methionine using a yeast having production capability of S-adenosyl-L-methionine, the method containing: adding a cyclodextrin compound to a yeast concentrate obtained from a fungus culture liquid of the yeast; and then drying the concentrate.

(2) The method for producing a dry yeast containing S-adenosyl-L-methionine according to the item (1), wherein the yeast having production capability of S-adenosyl-L-methionine is a yeast belonging to *Saccharomyces*.

(3) The method for producing a dry yeast containing S-adenosyl-L-methionine according to the item (2), wherein the yeast belonging to *Saccharomyces* is *Saccharomyces cerevisiae*.

(4) The method for producing a dry yeast containing S-adenosyl-L-methionine according to the item (1), wherein the cyclodextrin compound added is α-, β- or γ-cyclodextrin or a derivative thereof.

(5) The method for producing a dry yeast containing S-adenosyl-L-methionine according to the item (1), wherein an amount of the cyclodextrin compound added is in a range of from 0.05 to 6 times by mol based on SAMe contained in the separated concentrate of the yeast.

(6) The method for producing a dry yeast containing S-adenosyl-L-methionine according to the item (1), wherein the cyclodextrin compound added is γ-cyclodextrin.

(7) A dry yeast containing S-adenosyl-L-methionine produced by the method according to one of the items (1) to (6).

(8) A composition containing the dry yeast containing S-adenosyl-L-methionine according to the item (7), having been molded.

BEST MODE FOR CARRYING OUT THE INVENTION

The kind of the yeast used in the present invention may be one having production capability of SAMe and capable of being orally ingested, and examples thereof include yeasts belonging to *Saccharomyces*. Among these, *Saccharomyces cerevisiae* is more preferred. A dry yeast contains large amounts of useful components, such as 5'-nucleotide, a free amino acid, glutathione having antioxidant action and capability of improving hepatic function, β-glucan having function of enhancing immune strength and function of regulating intestinal function, and dietary fibers, and is used widely as health foods.

A carbon source used for culturing the yeast is not particularly limited as far as it is capable of being utilized by the yeast, and examples thereof include a hydrocarbon, such as glucose, sucrose, starch and blackstrap molasses, an alcohol, such as ethanol, and an organic acid, such as acetic acid. A nitrogen source therefor is also not particularly limited as far as it is capable of being utilized by the yeast, and examples thereof include an inorganic nitrogen compound, such as ammonia, nitric acid and urea, and those containing an organic nitrogen compound, such as yeast extract and malt extract. Examples of an inorganic salt therefor include salts of a phosphoric acid, potassium, sodium, magnesium, calcium, iron, zinc, manganese, cobalt, copper and molybdenum. Furthermore, the culture may be performed by adding methionine, adenine and adenosyl ribonucleoside constituting the skeleton of SAMe.

While the culture temperature and the pH of the culture liquid vary depending on the kind of the yeast, the culture temperature may be in a range of from 20 to 35° C., and the pH of the culture liquid may be in a range of from 4 to 7.

Aerobic culture is preferred for increasing the SAMe content in the fungus. The culture vessel may be one that can be aerated and can be stirred depending on necessity, and for example, a mechanically stirred culture vessel, an air-lift type culture vessel, a bubble tower type culture vessel and the like may be used.

As the feeding method of the culture medium, a carbon source, a nitrogen source, various inorganic salts, various additives and the like may be fed at one time or individually and continuously or intermittently. For example, a substrate, such as sucrose and ethanol, may be fed to the culture vessel in the form of a mixture with other components of the culture medium, or may be independently added to the culture vessel separately from the other components of the culture medium. The pH of the culture liquid can be controlled with an acid or alkali solution. The alkali for controlling the pH is preferably ammonia and urea, which are used as the nitrogen source, or a non-nitrogen base, such as sodium hydroxide and potassium hydroxide. Examples of the acid used include an inorganic acid, such as phosphoric acid, sulfuric acid and nitric acid, and an organic acid. A phosphate salt, a potassium salt, a sodium salt, a nitrate salt and the like, which are inorganic bases, may be used for controlling the pH.

The yeast is cultured under the conditions, and in the stage where the target amount of SAMe is accumulated in the yeast, the culture liquid is taken out, from which the yeast is separated. The separating method is not particularly limited as far as the fungus can be separated and rinsed efficiently, and preferred examples thereof include a counter current yeast separator and an ultrafiltration apparatus using a separation membrane.

Subsequently, a cyclodextrin compound is added to the separated concentrate of the yeast separated, for example, at room temperature in the form of powder or an aqueous solution, and the mixture is stirred for a prescribed period of time and then dried. According to the procedure, SAMe in the dry yeast is enhanced in storage stability, and an abnormal odor like sulfurous smell accompanied with storage can be suppressed from being generated. Furthermore, the yield of SAMe in the drying step of the yeast is improved, and the odor peculiar to the dry yeast is masked. The amount of cyclodextrin compound added is preferably in a range of from 0.05 to 6 times by mol, more preferably a range of from 0.1 to 4 times by mol, and further preferably a range of from 0.5 to 4 times by mol, based on SAMe contained in the separated concentrate of the yeast, from the standpoint of storage stability of SAMe in the dry yeast.

Examples of the cyclodextrin compound used in the present invention include α-, β- or γ-cyclodextrin and a derivative thereof, and among these, γ-cyclodextrin is particularly effective. The cyclodextrin compound may be used solely or as a mixture of two or more kinds thereof. Examples of the derivative include glucosylcyclodextrin, maltosylcyclodextrin, hydroxypropylcyclodextrin, methylated cyclodextrin and dimethylated cyclodextrin. The cyclodextrin compound is commonly used in the form of powder, granules or crystals in the fields of food, cosmetics and medicines, and can be used safely.

After adding the cyclodextrin compound, the water content is evaporated from the resulting yeast concentrate, for example, by such a drying method as a spray drying method with a spray dryer and a freeze drying method, thereby providing a dry yeast. As for the drying conditions in the spray drying method, the concentrate is preferably dried at an inlet temperature of 210° C. or less and an outlet temperature of 110° C. or less. In the freeze drying method, the concentrate is preferably dried at a final stage temperature of 30° C. or less. The SAMe-containing dry yeast of the present invention preferably has a water content of 5.0% by mass or less from the standpoint of storage stability thereof.

Furthermore, the dry yeast may be pulverized to powder, and another bioactive component and an additive, such as a vehicle, may be added to the dry yeast in the form of powder if needed, which may be then tabletted by compression to provide a composition in the form of tablet, the surface of which may be coated. The powder may be granulated into a granular form, and the powder or the granules thus granulated may be capsulated.

EXAMPLE

The present invention will be described in more detail with reference to examples and comparative examples, but the present invention is not limited to the examples.

Examples 1 to 6

(a) Culture of Yeast

According to the known culture method (Schlenk F., DePalma R. E., J. Biol. Chem., 229, 1037-1050 (1957) (Non-patent Document 1) and Shiozaki S., et al, Agric. Biol. Chem., 53, 3269-3274 (1989) (Non-patent Document 3)), Yeast *saccharomyces cerevisiae* IFO 2346 belonging to *Saccharomyces* was inoculated in a culture medium containing L-methionine (Shiozaki S. et al, J. Biotechnology, 4, 345-354 (1986) (Non-patent Document 6)), and cultured at a culture temperature of from 27 to 29° C. and stirred under aerophilic aeration for 6 days. Consequently, 18 L of a yeast culture liquid having a fungus content of 3.5% by mass and a SAMe content of 205 mg per gram of dry yeast was obtained.

(b) Collection of Yeast

18 L of the yeast culture liquid was treated with a continuous rotary type centrifugal separator (Hitachi Himac Centrifuge CR10B2) to provide 3.4 kg of a yeast concentrate in the form of liquid having a fungus concentration corresponding to 18% by mass in terms of dry product.

(c) Addition of Cyclodextrin Compound to Yeast Concentrate

γ-Cyclodextrin was added to 3.4 kg of the yeast concentrate in an amount of 0.1, 0.5, 1.0, 2.0, 3.0 or 4.0 times by mol based on SAMe in the yeast concentrate, and stirred and mixed at room temperature for 30 minutes, thereby providing a yeast concentrate having γ-cyclodextrin added thereto.

(d) Production of Dry Yeast

The yeast concentrate having γ-cyclodextrin added thereto was poured into a stainless steel tray for freeze drying of a freeze dryer (produced by ULVAC, Inc.) and frozen at −50° C., and then freeze dried for 36 hours under conditions of a final stage temperature of 25° C. The resulting freeze dried yeast was further pulverized to provide a powder dry yeast. The powder dry yeast thus obtained was charged in a sealed glass vessel and tested for storage stability under an acceleration condition of 40° C. and 75% RH. The results obtained are shown in Table 1. The residual rate of SAMe was measured in such a manner that SAMe was extracted from the SAMe-containing dry yeast by a known method using perchloric acid (see, for example, Non-patent Document 2) and quantitatively determined with liquid chromatography. The presence of an odor after storing was tested by a sensory test with five subjects. For the measurement method of SAMe in the present invention, liquid chromatography under the following analysis conditions was used.
Conditions Used:
Column: Nacalai Tesque, Inc., Cosmosil 4.6 mm in diameter× 100 mm
Eluant: 0.2M $KH_2PO_4$ aqueous solution/methanol=95/5
Flow rate: 0.7 mL/min
Detector: UV (260 nm)
SAMe retention time: ca. 150 seconds Examples 7 to 12

Powder dry yeasts were obtained in the same manner as in Example 1, but β-cyclodextrin was used with the yeast concentrate. The SAMe contents in the resulting powder dry yeasts, the amounts of β-cyclodextrin added, the results of storage stability test of the resulting SAMe-containing dry yeasts in the sealed glass vessel under an acceleration condition of 40° C. and 75% RH, and the results of the sensory test are shown in Table 1.

Examples 13 to 17

Powder dry yeasts were obtained in the same manner as in Example 1 except that α-cyclodextrin was added to the yeast concentrate in an amount of 0.5, 1.0, 2.0, 3.0 or 4.0 times by mol based on SAMe in the yeast concentrate. The SAMe contents of the resulting powder dry yeasts, the amounts of α-cyclodextrin added, the results of storage stability test of the resulting SAMe-containing dry yeasts in the sealed glass vessel under an acceleration condition of 40° C. and 75% RH, and the results of the sensory test are shown in Table 1.

Examples 18 and 19

The operations (a) to (b) were performed in the same manner as in Example 1, and γ-cyclodextrin or β-cyclodextrin was added to the resulting liquid yeast concentrate in an amount of 2.0 times based on SAMe and stirred and dissolved at room temperature for 30 minutes, thereby providing a yeast concentrate having γ-cyclodextrin dissolved therein and a yeast concentrate having β-cyclodextrin dissolved therein. The yeasts were each spray dried with a spray dryer having a two-fluid nozzle as an atomizing device under a condition of an inlet temperature of the drying chamber of 145° C., an outlet temperature thereof of 85° C. and a liquid feeding rate of 1.5 g/min, thereby providing powder dry yeasts. The SAMe contents of the resulting powder yeasts, the amounts of the additives, the results of storage stability test of the resulting SAMe-containing dry yeasts in the sealed glass vessel under an acceleration condition of 40° C. and 75% RH, and the results of the sensory test are shown in Table 1.

Comparative Example 1

A powder dry yeast was obtained in the same manner as in Example 1 except that no cyclodextrin compound was added to the yeast concentrate. The SAMe content of the resulting powder dry yeast, the results of storage stability test of the resulting SAMe-containing dry yeast in the sealed glass vessel under an acceleration condition of 40° C. and 75% RH, and the results of the sensory test are shown in Table 1.

Comparative Example 2

A powder dry yeast was obtained in the same manner as in Example 1 except that starch was added to the yeast concentrate in an amount of 5.0% by mass based on the yeast concentrate. The SAMe content of the resulting powder dry yeast, the amount of starch added, the results of storage stability test of the resulting SAMe-containing dry yeast in the sealed glass vessel under an acceleration condition of 40° C. and 75% RH, and the results of the sensory test are shown in Table 2.

Comparative Example 3

A powder dry yeast was obtained in the same manner as in Example 1 except that dextrin hydrate was added to the yeast concentrate in an amount of 10% by mass based on the yeast concentrate. The SAMe content of the resulting powder dry yeast, the amount of dextrin hydrate added, the results of storage stability test of the resulting SAMe-containing dry yeast in the sealed glass vessel under an acceleration condition of 40° C. and 75% RH, and the results of the sensory test are shown in Table 2.

Comparative Example 4

A powder dry yeast was obtained in the same manner as in Example 1 except that sucrose was added to the yeast concentrate in an amount of 1.0 equivalent by mol based on SAMe in the yeast concentrate. The SAMe content of the resulting powder dry yeast, the amount of sucrose added, the results of storage stability test of the resulting SAMe-containing dry yeast in the sealed glass vessel under an acceleration condition of 40° C. and 75% RH, and the results of the sensory test are shown in Table 2.

Comparative Example 5

A powder dry yeast was obtained in the same manner as in Example 1 except that maltose was added to the yeast concentrate in an amount of 1.0 equivalent by mol based on SAMe in the yeast concentrate. The SAMe content of the resulting powder dry yeast, the amount of maltose added, the results of storage stability test of the resulting SAMe-containing dry yeast in the sealed glass vessel under an acceleration condition of 40° C. and 75% RH, and the results of the sensory test are shown in Table 2.

Comparative Example 6

A powder dry yeast was obtained in the same manner as in Example 1 except that glucose was added to the yeast concentrate in an amount of 1.0 equivalent by mol based on SAMe in the yeast concentrate. The SAMe content of the resulting powder dry yeast, the amount of glucose added, the results of storage stability test of the resulting SAMe-containing dry yeast in the sealed glass vessel under an acceleration condition of 40° C. and 75% RH, and the results of the sensory test are shown in Table 2.

Comparative Example 7

A powder dry yeast was obtained in the same manner as in Example 1 except that xylitol was added to the yeast concentrate in an amount of 1.0 equivalent by mol based on SAMe in the yeast concentrate. The SAMe content of the resulting powder dry yeast, the amount of xylitol added, the results of storage stability test of the resulting SAMe-containing dry yeast in the sealed glass vessel under an acceleration condition of 40° C. and 75% RH, and the results of the sensory test are shown in Table 2.

TABLE 1

Results of storage stability test of SAMe-containing dry yeasts in sealed glass vessel under acceleration condition of 40° C. and 75% RH

| Example | Additive *1 | Amount of additive contained in dry yeast (%) | Amount of additive based on SAMe in yeast concentrate (molar ratio) | SAMe content in dry yeast at start of test (% by mass) | Storage stability test (SAMe residual rate in SAMe-containing yeast (%)) Elapsed days | | | | Presence of abnormal odor after 60 days *2 |
|---|---|---|---|---|---|---|---|---|---|
| | | | | | After 15 days | After 30 days | After 45 days | After 60 days | |
| Comparative Example 1 | none | 0 | 0 | 16.5 | 54.7 | 23.5 | 0.0 | 0.0 | C |
| Example 1 | γ-CD | 5.1 | 0.1 | 15.7 | 63.8 | 34.8 | 0.0 | 0.0 | B |
| Example 2 | " | 21.2 | 0.5 | 13.0 | 99.9 | 99.7 | 99.4 | 84.2 | A |
| Example 3 | " | 34.9 | 1.0 | 10.8 | 99.8 | 99.8 | 99.5 | 96.5 | A |
| Example 4 | " | 51.8 | 2.0 | 8.0 | 99.9 | 99.9 | 99.6 | 98.7 | A |
| Example 5 | " | 61.7 | 3.0 | 6.3 | 99.8 | 99.9 | 99.7 | 98.4 | A |
| Example 6 | " | 68.2 | 4.0 | 5.3 | 99.9 | 99.8 | 99.6 | 98.5 | A |
| Example 7 | β-CD | 4.5 | 0.1 | 15.8 | 59.8 | 24.5 | 0.0 | 0.0 | B |
| Example 8 | " | 19.0 | 0.5 | 13.4 | 99.9 | 99.7 | 99.5 | 54.2 | A |
| Example 9 | " | 32.0 | 1.0 | 11.2 | 99.8 | 99.7 | 99.7 | 58.7 | A |

TABLE 1-continued

Results of storage stability test of SAMe-containing
dry yeasts in sealed glass vessel under acceleration condition
of 40° C. and 75% RH

| Example | Additive *1 | Amount of additive contained in dry yeast (%) | Amount of additive based on SAMe in yeast concentrate (molar ratio) | SAMe content in dry yeast at start of test (% by mass) | Storage stability test (SAMe residual rate in SAMe-containing yeast (%)) Elapsed days | | | | Presence of abnormal odor after 60 days *2 |
|---|---|---|---|---|---|---|---|---|---|
| | | | | | After 15 days | After 30 days | After 45 days | After 60 days | |
| Example 10 | " | 48.4 | 2.0 | 8.5 | 99.8 | 99.9 | 99.6 | 62.8 | A |
| Example 11 | " | 58.5 | 3.0 | 6.9 | 99.9 | 99.8 | 99.6 | 69.5 | A |
| Example 12 | " | 65.3 | 4.0 | 5.7 | 99.8 | 99.9 | 99.7 | 68.1 | A |
| Example 13 | α-CD | 16.8 | 0.5 | 13.8 | 99.9 | 99.7 | 99.3 | 57.3 | A |
| Example 14 | " | 28.7 | 1.0 | 11.8 | 99.8 | 99.9 | 99.5 | 62.4 | A |
| Example 15 | " | 44.6 | 2.0 | 9.2 | 99.8 | 99.8 | 99.6 | 68.5 | A |
| Example 16 | " | 54.7 | 3.0 | 7.5 | 99.8 | 99.9 | 99.7 | 68.2 | A |
| Example 17 | " | 61.7 | 4.0 | 6.3 | 99.8 | 99.8 | 99.5 | 67.8 | A |
| Example 18 | γ-CD | 51.8 | 2.0 | 8.0 | 99.9 | 99.9 | 99.6 | 98.7 | A |
| Example 19 | β-CD | 48.4 | 2.0 | 8.5 | 99.8 | 99.9 | 99.6 | 62.8 | A |

*1: Examples 1 to 6: γ-cyclodextrin (γ-CD) added (drying method: freeze drying)
*1: Examples 7 to 12: β-cyclodextrin (β-CD) added (drying method: freeze drying)
*1: Examples 13 to 17: α-cyclodextrin (α-CD) added (drying method: freeze drying)
*1: Example 18: γ-cyclodextrin (γ-CD) added (drying method: spray drying)
*1: Example 19: β-cyclodextrin added (drying method: spray drying)
*2: Sensory test: A: no abnormal odor, B: slight abnormal odor, C: abnormal odor present

TABLE 2

Results of storage stability test of SAMe-containing
dry yeasts in sealed glass vessel under acceleration condition
of 40° C. and 75% RH

| Example | Additive | Amount of additive contained in dry yeast (%) | Amount of additive based on SAMe in yeast concentrate (molar ratio) | SAMe content in dry yeast at start of test (% by mass) | Storage stability test (SAMe residual rate in SAMe-containing yeast (%)) Elapsed days | | | | Presence of abnormal odor after 60 days* |
|---|---|---|---|---|---|---|---|---|---|
| | | | | | After 15 days | After 30 days | After 45 days | After 60 days | |
| Comparative Example 2 | starch | 15.0 | — | 13.8 | 58.1 | 28.2 | 0.0 | 0.0 | C |
| Comparative Example 3 | dextrin hydrate | 15.0 | — | 13.8 | 59.4 | 27.0 | 0.0 | 0.0 | C |
| Comparative Example 4 | sucrose | 14.0 | 1.0 | 12.0 | 49.8 | 11.8 | 0.0 | 0.0 | C |
| Comparative Example 5 | maltose | 12.5 | 1.0 | 14.6 | 47.2 | 23.1 | 0.0 | 0.0 | C |
| Comparative Example 6 | glucose | 6.8 | 1.0 | 14.9 | 47.9 | 27.3 | 0.0 | 0.0 | C |
| Comparative Example 7 | xylitol | 5.8 | 1.0 | 14.9 | 62.3 | 33.3 | 0.0 | 0.0 | C |

*Sensory test: A: no abnormal odor, B: slight abnormal odor, C: abnormal odor present

INDUSTRIAL APPLICABILITY

The use of the production method of the present invention enables production of a dry yeast containing SAMe in a high concentration capable of being stored stably and a composition formed by molding the same with a simple process. Accordingly, SAMe useful as a physiologically active substance for medical drugs and health foods can be brought into the market thereby at an economical price.

The invention claimed is:

1. A method for producing a dry yeast composition containing both S-adenosyl-L-methionine ("SAMe") and a cyclodextrin compound comprising:
   culturing a yeast that produces S-adenosyl-L-methionine in a culture medium to a point where S-adenosyl-L-methionine is accumulated inside the yeast and separating the yeast containing S-adenosyl-L-methionine from the culture medium;
   adding a cyclodextrin compound to the yeast separated from the culture medium before drying; and then
   drying the mixture of the yeast and the cyclodextrin compound, thus producing a dry yeast composition containing both S-adenosyl-L-methionine and the cyclodextrin compound;
   wherein the molar amount of the cyclodextrin compound added ranges from 0.5 to 6 times the molar amount of S-adenosyl-L-methionine in the yeast which was separated from the liquid it was cultured in.

2. The method according to claim 1, wherein the yeast having production capability of S-adenosyl-L-methionine is a yeast belonging to *Saccharomyces*.

3. The method according to claim 2, wherein the yeast belonging to *Saccharomyces* is *Saccharomyces cerevisiae*.

4. The method of claim 1, wherein the yeast is separated from the culture medium by a counter current yeast separator.

5. The method of claim 1, wherein the yeast is separated from the culture by ultrafiltration.

6. The method of claim 1, wherein said drying comprises spray drying.

7. The method of claim 1, wherein said drying comprises freeze-drying.

8. The method of claim 1, wherein said adding a cyclodextrin compound to the yeast consists of adding dry cyclodextrin or an aqueous solution of cyclodextrin to the yeast prior to drying.

9. The method of claim 1, wherein said yeast that can produce S-adenosyl-L-methionine is separated from liquid it was cultured in, rinsed and resuspended in a liquid prior to addition of cyclodextrin.

10. A method for making a dry yeast composition comprising dry yeast cells containing inside them S-adenosyl-L-methionine and a cyclodextrin compound, comprising:
    culturing a yeast that produces S-adenosyl-L-methionine in a culture medium to a point where S-adenosyl-L-methionine is accumulated inside the yeast;
    separating the yeast containing S-adenosyl-L-methionine from the culture medium;
    determining a molar amount of S-adenosyl-L-methionine in the yeast cells separated from the culture medium;
    adding a cyclodextrin compound in an amount ranging from 0.5 to 6 times the molar amount of S-adenosyl-L-methionine inside the separated yeast before drying; and then
    drying the mixture of the yeast and the cyclodextrin compound to produce a composition containing dry yeast cells with S-adenosyl-L-methionine inside them, and the cyclodextrin compound;
    wherein the S-adenosyl-L-methionine in said composition is more stable than that in an otherwise identical composition made by an otherwise identical method that does not add cyclodextrin prior to drying after storage in a sealed glass vessel at 40° C. at 75% relative humidity for 15 days.

11. The method of claim 10, further comprising rinsing the yeast containing S-adenosyl-L-methionine, which were separated from the culture medium, prior to adding the cyclodextrin and prior to drying.

12. The method of claim 10, wherein adding a cyclodextrin compound in an amount ranging from 0.5 to 6 times the molar amount of S-adenosyl-L-methionine inside the separated yeast before drying consists essentially of adding cyclodextrin to the separated yeast cells immediately before drying.

13. The method according to claim 1, wherein the cyclodextrin compound added is a-cyclodextrin or a derivative thereof.

14. The method according to claim 1, wherein the cyclodextrin compound added is β-cyclodextrin or a derivative thereof.

15. The method according to claim 1, wherein the cyclodextrin compound added is γ-cyclodextrin or a derivative thereof.

16. The method according to claim 1, wherein more of the S-adenosyl-L-methionine in the dry yeast composition, which contains both S-adenosyl-L-methionine and the cyclodextrin compound, is present after 60 days than is present in an otherwise identical dry yeast composition containing starch, dextrin hydrate, sucrose, glucose or xylitol instead of cyclodextrin.

17. The method according to claim 1, wherein the yeast separated from the culture medium when dry contains 5.3 to 20.5% SAMe content by mass.

18. The method according to claim 1, wherein the yeast separated from the culture medium contains 10.8 to 20.5% SAMe content by mass.

19. The method according to claim 1, wherein the yeast that produces S-adenosyl-L-methionine has been transformed with a SAMe-synthesizing gene.

* * * * *